United States Patent [19]
Tsuchiya et al.

[11] Patent Number: 5,178,515
[45] Date of Patent: Jan. 12, 1993

[54] MEDICAL PUMP

[75] Inventors: Kiichi Tsuchiya, Tokyo; Nobuyuki Kabei, Chiba; Ryouichi Konou, Hachioji, all of Japan

[73] Assignee: Olympus Optical Co., Ltd., Tokyo, Japan

[21] Appl. No.: 798,369

[22] Filed: Nov. 21, 1991

Related U.S. Application Data

[63] Continuation of Ser. No. 489,328, Mar. 5, 1990, abandoned.

[30] Foreign Application Priority Data

May 22, 1989 [JP] Japan ................................. 1-128322

[51] Int. Cl.$^5$ .............................................. F04D 29/18
[52] U.S. Cl. ................................. 415/206; 415/900; 416/223 B; 600/16; 623/3
[58] Field of Search ................ 415/203, 206, 900; 416/181, 223 B, 231 A; 600/16, 17; 623/3

[56] References Cited

U.S. PATENT DOCUMENTS

| | | | |
|---|---|---|---|
| 1,884,067 | 10/1932 | Melos | 416/231 B |
| 2,107,090 | 2/1938 | Swennes | 415/229 |
| 2,956,503 | 10/1960 | Neidl | 416/223 B |
| 3,647,324 | 3/1972 | Rafferty et al. | 415/900 |
| 3,702,938 | 11/1972 | Garnier | 415/90 |
| 4,135,253 | 1/1979 | Reich et al. | |

FOREIGN PATENT DOCUMENTS

| | | | |
|---|---|---|---|
| 1258114 | 2/1961 | France | 415/143 |
| 57-170746 | 4/1956 | Japan | |
| 96197 | 8/1981 | Japan | 415/122.1 |
| 57-145667 | 9/1982 | Japan | |
| 57-168672 | 10/1982 | Japan | |

OTHER PUBLICATIONS

Vol. XXXII, Trans Am Soc Artif Intern Organs 1986, "Investigation of the Flow in a Centrifugal Blood Pump", by Klaus Affeld et al.; pp. 269-273.
"Fluid-Dynamical Characteristics of a Modified Tea-Spoon Type Centrifugal Blood Pump", T. Shiroyama et al., Mar. 14, 1985, pp. 1130-1132.
"Improvement of Performance of Nutating Centrifugal Blood Pump and Simulation of its Hemolysis Test", T. Shiroyama et al., Feb. 18, 1989, pp. 551-554.
"Trend of Development of Artificial Heart-Its Structure and Functions", Jour. JSME, vol. 92, pp. 198-205.

Primary Examiner—John T. Kwon
Attorney, Agent, or Firm—Frishauf, Holtz, Goodman & Woodward

[57] ABSTRACT

A medical pump comprises a casing having side walls, a peripheral wall, and a pump chamber defined thereby, an inlet port formed substantially in the central portion of one of the side walls of the casing, an outlet port formed in the peripheral wall of the casing so as to extend tangent thereto, a rocker substantially concentric with the inner peripheral surface of the casing and disposed in the chamber, and a rocker driving unit for rocking the rocker so as to vary the volume of the space between the rocker and the outlet port with the lapse of time, thereby producing a rotating flow in fluid in the casing.

9 Claims, 15 Drawing Sheets

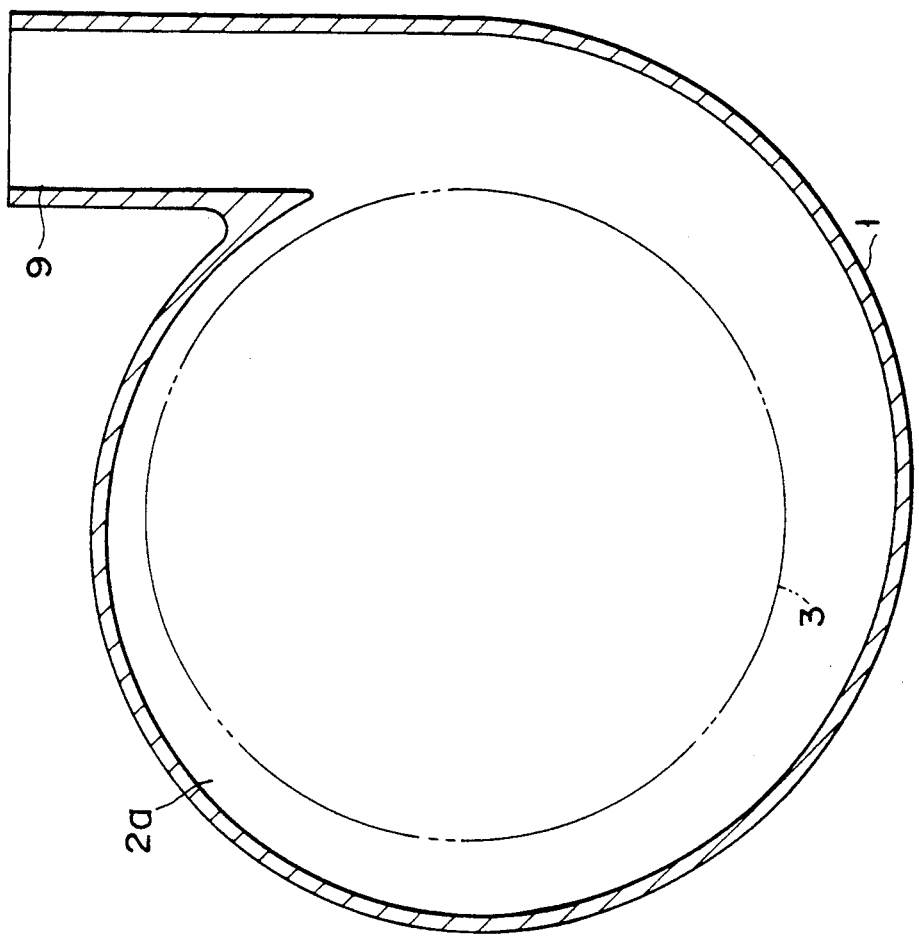
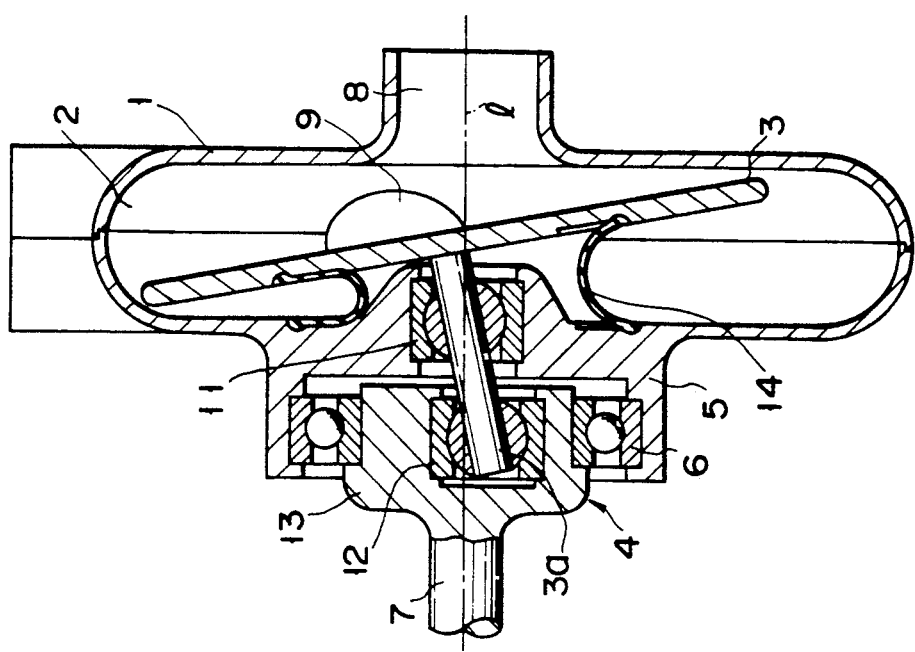
F I G. 2
F I G. 1

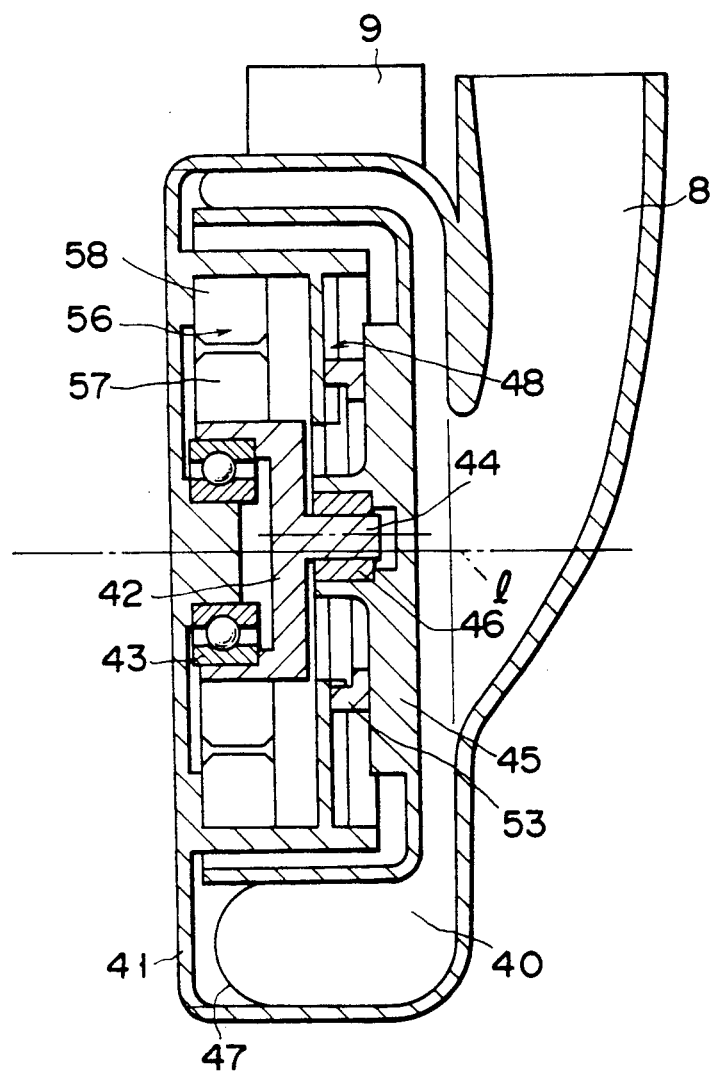
F I G. 6

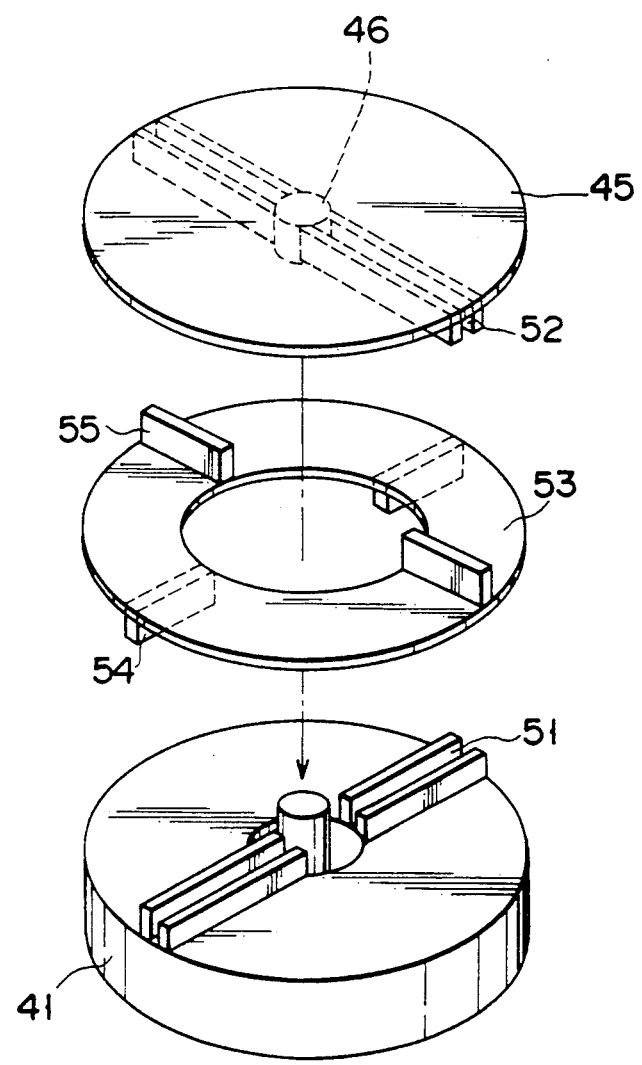
F I G. 7

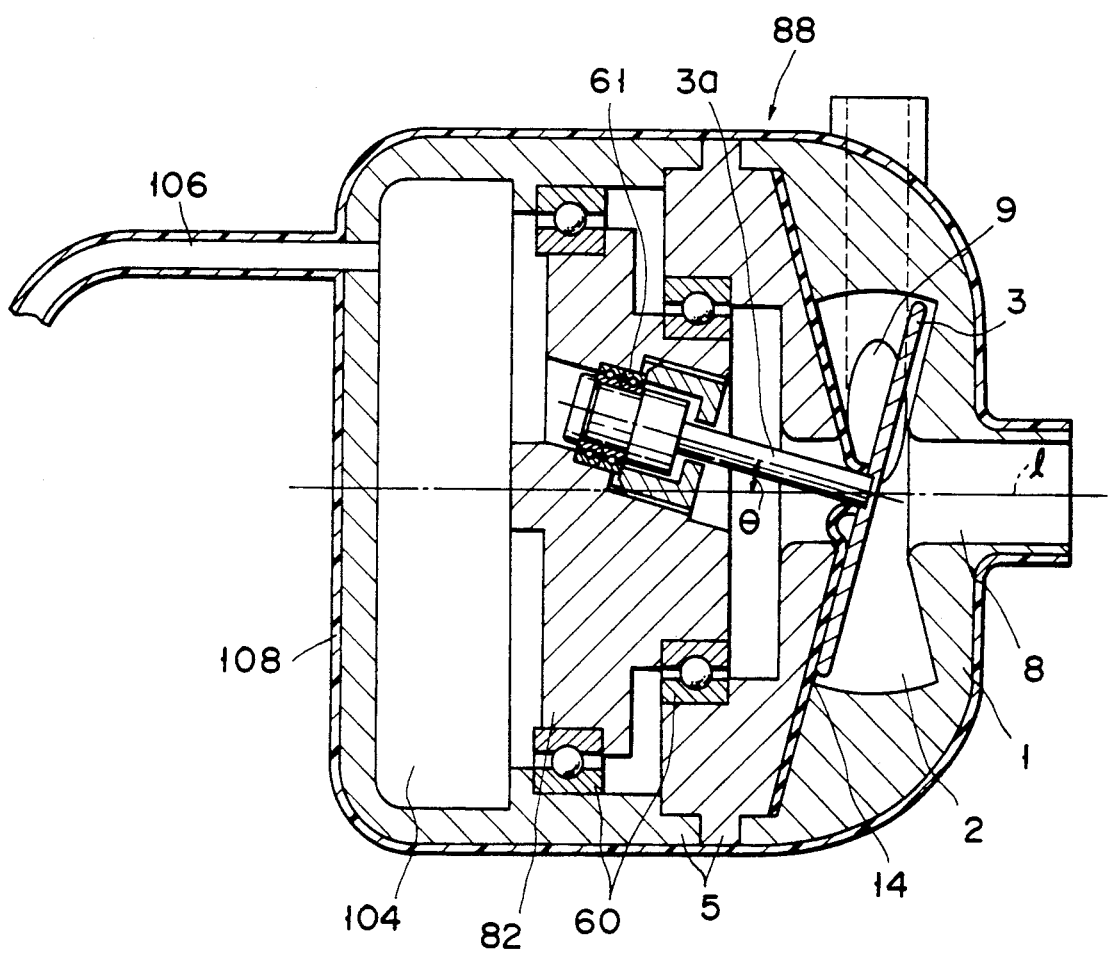
F I G. 18

MEDICAL PUMP

This application is a continuation of application Ser. No. 07/489,328, filed Mar. 5, 1990 now abandoned.

BACKGROUND OF THE INVENTION

1. Field of the Invention

The present invention relates to a medical pump adapted for use as a blood pump for a heart-lung machine, blood pump as a substitute for the heart, auxiliary heart, artificial heart, etc.

2. Description of the Related Art

Pumps of various types have already been developed as blood pumps for medical use. These pumps include, for example, roller pumps, finger pumps, positive-displacement blood pumps, rotary blood pumps, centrifugal pumps, and teaspoon-type centrifugal pumps (see "Artificial Organs" Vol. 18, No. 2, pp. 448 to 452). In the roller pumps, blood in an elastic tube is gradually forced out for delivery by stroking the tube by means of a roller. In the finger pumps, blood in an elastic tube is forced out by gradually constricting the tube by means of a compressor. In the positive-displacement pumps, blood is sucked in or pulsed out by reciprocating a piston or diaphragm by means of a check valve at the inlet or outlet. In the rotary pumps, blood is discharged by rotating a rotor to change the capacity of a space between the rotor and a pump housing. In the centrifugal pumps, an impeller is rotated at high speed to apply a centrifugal force to blood, thereby discharging the blood. In the teaspoon pumps, a blade is brought into precession.

According to the roller pumps or finger pumps in which blood is discharged by stroking or constricting the elastic tube, however, blood cells of the blood are liable to be destroyed (or hemolyzed), so that the pumps can hardly stand prolonged use. Since the deformation of the elastic tube requires a lot of energy, moreover, the efficiency of energy conversion is low.

In the positive-displacement pumps, the artificial valve located at the inlet or outlet is very expensive, and blood is liable to coagulate around the valve. Since one pulse requires a capacity equivalent to that of the heart, moreover, the artificial heart, including a drive mechanism therefor, has so large a total capacity that it cannot be easily implanted in the thoracic cavity. Since the internal diaphragm is reciprocated, furthermore, the energy conversion efficiency is lower than in the case of the rotary pumps.

In the rotary pumps, blood is liable to be destroyed by the rotor, and microbism or blood coagulation can be easily caused unless the gap between a rotating shaft and a housing section is fully sealed. Satisfactory sealing between the shaft and the housing section, however, requires engineering skill of a high order.

In the centrifugal pumps, the gap between the rotating shaft and the housing section cannot be fully sealed. In order to solve this problem of sealing, the drive mechanism and the impeller may be magnetically coupled through a housing wall by the use of a permanent magnet. According to this method, however, the pump section must be increased in size, and the energy conversion efficiency is extremely low.

The teaspoon pumps have been developed to cope with these problems. These pumps are based on the principle that a fluid in a vessel can be rotated by bringing a spoon into precession. More specifically, a spoon-shaped blade, having spindle-shaped cut end portions, is caused to make a precessional motion in a casing, thereby fulfilling a turbo-pump function.

In these teaspoon pumps, however, blood at the outer peripheral portion of a pump chamber is stirred by means of the spoon so that the blood is delivered centrifugally. Therefore, the configuration of a passage is so complicated that the manufacture of the pump is difficult and entails higher costs.

Since the single spoon-shaped blade is used in the teaspoon pumps, moreover, the energy conversion efficiency is low.

If the pump chamber is formed into an annular passage through which the blade passes, in order to improve the energy conversion efficiency, the gap between the blade and the wall surface of the annular passage is so narrow that a great shearing force is applied to blood cells of the blood flowing through the gap, thereby causing substantial hemolysis. Since the blood flow near the root of the spoon involves no substantial kinetic energy, moreover, the blood may possibly coagulate at that portion after prolonged use.

In general, blood pumps for medical use are expected to have all of such advantages as reluctance to cause destruction or coagulation of blood, small capacity, high energy conversion efficiency, etc.

SUMMARY OF THE INVENTION

The object of the present invention is to provide a medical pump capable of efficiently feeding a fluid by producing a rotating flow in the fluid in a pump chamber by means of a rocker which rocks in the pump chamber.

The above object of the present invention is achieved by a medical pump constructed as follows. The medical pump comprises a casing having side walls, a peripheral wall, and a pump chamber defined thereby, an inlet port formed substantially in the central portion of one of the side walls of the casing, an outlet port formed in the peripheral wall of the casing so as to extend tangent thereto, rocker means substantially concentric with the inner peripheral surface of the casing and disposed in the chamber, and rocker driving means for rocking the rocker means so as to vary the volume of the space between the rocker means and the outlet port with the lapse of time, thereby producing a rotating flow in fluid in the chamber.

In the medical pump according to the present invention, a rocker is rocked without rotating blades, so that blood cells cannot be easily destroyed during blood supply.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a longitudinal sectional view of a medical pump according to a first embodiment of the present invention;

FIG. 2 is a cross-sectional view of a casing shown in FIG. 1;

FIG. 6 is a longitudinal sectional view of a medical pump according to a second embodiment of the present invention;

FIG. 7 is an exploded perspective view showing an Oldham mechanism of the medical pump according to the second embodiment;

FIG. 18 is a longitudinal sectional view of the medical pump according to the modification of the fourth embodiment;

DETAILED DESCRIPTION OF THE PREFERRED EMBODIMENTS

Figure 3:
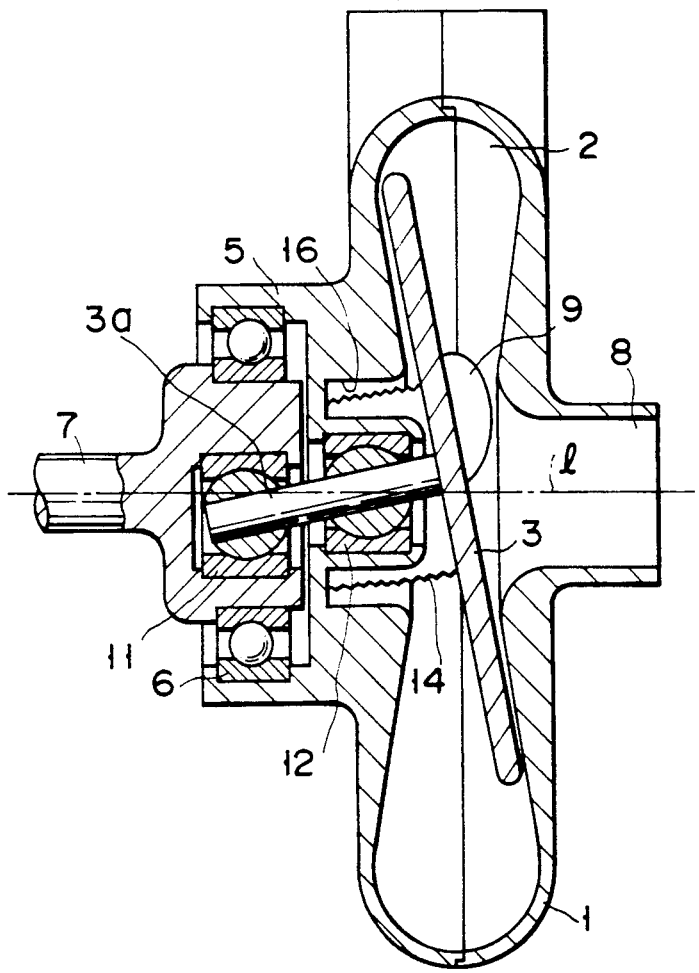
FIG. 3 is a longitudinal sectional view showing a first modification of the medical pump according to the first embodiment.

FIGS. 1 and 2 show a medical pump according to a first embodiment of the present invention. In FIGS. 1 and 2, numeral 1 denotes a substantially flat cylindrical casing which defines pump chamber 2 therein. Casing 1 has inlet port 8, situated near central axis 1 of chamber 2, and outlet port 9 extending tangent to the circumference of chamber 2. As shown in FIG. 2, passage 2a is formed at the peripheral portion of pump chamber 2. Passage 2a, which gradually recedes from the center of chamber 2, is continuous with outlet port 9. Thus, casing 1 is volute in shape.

Disk-shaped precessional rocker (disk) 3 is disposed in pump chamber 2. Rotating shaft 3a is attached to the center of rocker 3 so as to extend at right angles thereto. Rocker 3 is driven by means of precessional mechanism 4. The diameter of rocker 3 is substantially equal to that of casing 1 (or the shortest diameter of volute casing 1).

The following is a description of precessional mechanism 4. Bearing 6 is attached to body 5 which is integral with casing 1. The bearing 6 rotatably supports coupling portion 13 at the extreme end of motor shaft 7, which is connected to a motor (not shown). The proximal portion of rotating shaft 3a of rocker 3 is supported by first precessional bearing 11, which is attached to body 5 so as to be coaxial with motor shaft 7. The free end of shaft 3a is supported by second precessional bearing 12, which is eccentrically attached to coupling portion 13 at the extreme end of motor shaft 7.

In pump chamber 2, tubular seal 14, made of an elastic film such as rubber, is provided between casing 1 and rocker 3. Thus interposed between precessional mechanism 4 and rocker 3, seal 14 isolates pump chamber 2 from mechanism 4. The inner surface of casing 1 defining chamber 2 and the whole surface of rocker 3 are coated with an antithrombotic material.

The following is a description of the operation of the blood pump with the aforementioned construction. In the state shown in FIG. 1, rocker 3 in casing 1 is tilted in pump chamber 2. When the motor is driven to rotate motor shaft 7, second precessional bearing 12, which is eccentrically attached to the extreme end of shaft 7, makes an eccentric rotation. Thereupon, rotating shaft 3a of rocker 3 supported by bearing 12 is urged also to rotate around its central axis 1. Since shaft 3a is supported on axis 1 by means of first precessional bearing 11, moreover, rocker 3 is urged to rotate around bearing 11. However, the rotatory motion of rocker 3 is prevented by seal 14, so that rocker 3 makes a precessional motion around first precessional bearing 11.

As rocker 3 undergoes precession in this manner, the volume of the space between rocker 3 and outlet port 9 varies with the lapse of time, and a rotatory force acts on blood previously filled into pump chamber 2 of casing 1, so that the blood flows rotating in the same direction as the precessional motion. If the rotational frequency of motor shaft 7 is increased to about 1,000 to 3,000 rpm, the speed of the precessional motion of rocker 3 increases, and a substantial centrifugal force is produced in the blood, so that the blood gains great kinetic energy. Having the great kinetic energy, the blood flows to outlet port 9 through passage 2a at the peripheral portion inside casing 1, and is then discharged through port 9. As the blood moves toward outlet port 9, the pressure in the vicinity of inlet port 8 of casing 1 is lowered, so that blood is sucked in afresh.

As long as the blood is supplied through inlet port 8, it is given kinetic energy from rocker 3, thereby continuing to be discharged through outlet port 9. Thus, the blood pump fulfills its function as a turbo-type pump.

Since the diameter of rocker 3 is substantially equal to that of casing 1 (or the shortest diameter of volute casing 1), the working surface of the rocker has a considerable area. Thus, the blood can be subjected to sufficient rotatory energy from either side of rocker 3. The center of mass of the fluid between the obverse of rocker 3 and casing 1 is situated with a phase difference of 180° from that of the fluid between the reverse of rocker 3 and casing 1. Practically, therefore, rocker 3 can produce the same pumping effect of an impeller having two blades. Thus, the efficiency of energy conversion is relatively high.

Hemolysis can be restrained by widening the gap between the obverse of rocker 3. Since the blood also flows sufficiently on the reverse side of rocker 3, moreover, there is no region of low-speed flow in pump chamber 2. Thus, there is no possibility of blood coagulation, so that the pump can stand prolonged use.

Since the pump of the present invention is of the turbo-type, furthermore, pump chamber 2 can be reduced in capacity. Accordingly, the pump of the invention can be used as a miniature blood pump which can be easily implanted in a patient's body.

The precessional motion can be caused in rocker 3 by only continuously rotating the motor in the sam direction. Thus, the drive system for the pump is simple, and the energy conversion efficiency can be improved.

Also, the pump section has a simple construction, and the area of contact between mechanical parts and the blood is narrow. Accordingly, hemolysis or coagulation is not liable to take place.

FIG. 3 shows a first modification of the medical pump according to the first embodiment. In the description to follow, like members are designated by like reference numerals for simplicity.

In the medical pump shown in FIG. 3, pump chamber 2 defined in casing 1 has a profile such that its passage width is narrowest in the vicinity of inlet port 8 and gradually increases with distance from port 8. When rocker 3 undergoes a precessional motion, a narrow gap is left between the rocker and the wall surfaces of casing 1 which define chamber 2. Bellows-shaped seal 14, which is interposed between rocker 3 and casing 1, extends parallel to rotating shaft 3a of the rocker. One end portion of seal 14 is fitted in groove 16 in body 5 and is fixed to the wall of the body.

In the medical pump according to the first modification, the precessional motion of rocker 3 subjects the blood not only to a force in the rotating direction but also to a force in the direction parallel to central axis l. Accordingly, the blood flows toward the wall surfaces perpendicular to axis l while rotating and moving centrifugally. When the blood runs into the wall surfaces, it is redirected. Thus, in this modification, the wall surfaces perpendicular to central axis l of casing 1 are tilted so that pump chamber 2 becomes wider with distance from its central portion. According to this arrangement, the blood produces more centrifugal components of a force, and the energy of the blood flow can be more effectively utilized as a pump output.

Figure 4:
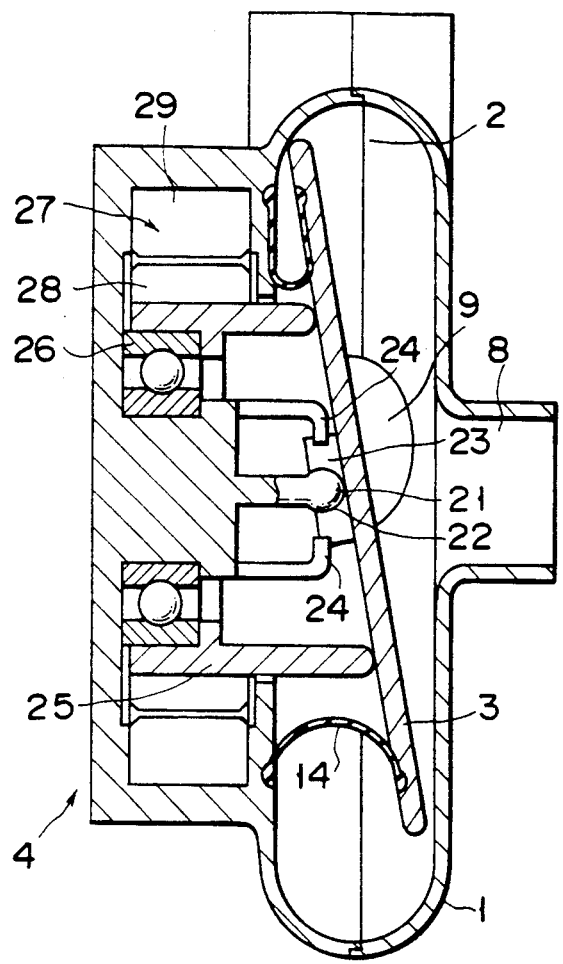
FIG. 4 is a longitudinal sectional view showing a second modification of the medical pump according to the first embodiment.
Figure 5:
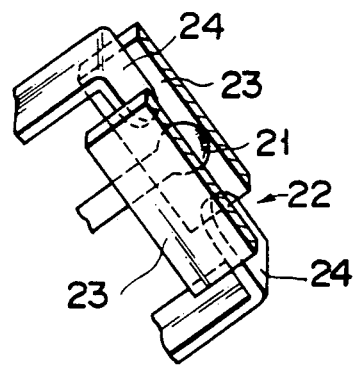
FIG. 5 is a perspective view of a combination of a spherical coupling and a holder shown in FIG. 4.

FIGS. 4 and 5 show a second modification of the first embodiment. In this modification, precessional mechanism 4 is modified. In pump chamber 2, as shown in FIG. 4, rocker 3 in the form of a disk is rockably supported by means of seal 14, but is kept from rotating.

Holder 22, which engages spherical coupling 21 protruding from casing 1, is attached to the central portion of rocker 3. Holder 22 allows rocker 3 to tilt in any direction around coupling 21. As shown in FIG. 5, holder 22 includes a pair of regulating plates 23, and a pair of regulating pins 24 protruding from casing 1 project between regulating plates 23 thereby preventing rocker 3 from rotating.

Further, rocker 3 is engagedly supported on a cam surface of inclined cylindrical cam 25 with an inclined end disposed in casing 1. As cam 25 rotates, the tilting direction of rocker 3 changes.

Inclined cylindrical cam 25 is supported on casing 1 by means of bearing 26. It is also fixed to rotor 28 of motor 27, which is contained in casing 1. Stator 29 of motor 27 is fixed to casing 1. When rotor 28 of motor 27 is rotated, therefore, rocker 3 is caused to make a precessional motion by means of cylindrical cam 25.

When rocker 3 makes the precessional motion in pump chamber 2, a rotatory force acts on the blood in chamber 2, so that the blood flows rotating in the same direction as the precessional motion. Thus given the rotatory energy, the blood flows to outlet port 9 and is then discharged through port 9. As the blood moves toward outlet port 9, the pressure in the vicinity of inlet port 8 of casing 1 is lowered, so that blood is sucked in afresh through port 8. As long as the blood is supplied through inlet port 8, it is given kinetic energy from rocker 3, thereby continuing to be discharged through outlet port 9. Thus, the blood pump fulfills its function as a turbo-type pump.

In the arrangement of this second modification, an energy source used to drive the pump, or an energy receiving section and a pump driving section may be contained in the pump, and the outer peripheral surface of the pump may be coated with a material having histocompatibility. By doing this, the pump can be used as an implantation-type blood pump.

FIGS. 6 and 7 show a second embodiment of the present invention. As shown in FIG. 6, casing 41 is in the form of a flat cylinder, and its peripheral portion is volute in shape. Rotating shaft 42 for rocking motion drive is rotatably supported on bearing 43 in casing 41. Shaft 42 is provided with driving pin 44 which projects eccentrically to central axis l. Pin 44 is connected to rocker 45 in pump chamber 40 by means of bearing 46.

Rocker 45 is formed of a cap having a central axis parallel to central axis l and a circular cross-sectional shape perpendicular thereto. In casing 41, two opposite ends of seal 47, made of an elastic film, are fixed individually to casing 41 and rocker 45. Seal 47 serves to seal the gap between casing 41 and rocker 45.

Rocker 45 is connected to casing 41 by means of Oldham mechanism 48, which resembles an Oldham coupling, so that it is prevented from rotating. Thus, mechanism 48 serves to restrain the rotation of rocker 45, and restrict the movement of the rocker to the directions of two perpendicular axes.

As shown in FIG. 7, casing 41 and rocker 45 are provided with groove portions 51 and 52, respectively, which extend at right angles to each other. Intermediate disk 53 is sandwiched between casing 4 and rocker 45. Disk 53 has projections 54, which engage groove portion 51 of casing 41, and projections 55 which engage groove portion 52 of rocker 45.

Rotor 57 of motor 56 is fixed to rotating shaft 42 for rocking motion drive. Stator 58 of motor 56 is fixed to casing 41.

If a current is applied to stator 58 of motor 56, rotor 57 rotates, so that rotating shaft 42 rotates. Although rocker 45, which is connected to shaft 42, is urged to circle round, its rotatory motion is limited by Oldham mechanism 48. As a result, rocker 45 rocks in pump chamber 40 in casing 41.

When rocker 45 rocks in pump chamber 40 in this manner, a rotatory force acts on the blood in chamber 40, so that the blood turns around. Thereupon, the blood is given kinetic energy, and is discharged through outlet port 9 of casing 41. If the blood is continuously supplied through inlet port 8 of casing 41, therefore, it is successively given kinetic energy as it flows through pump chamber 40 to outlet port 9. Then, the blood is discharged through port 9. Thus, the blood pump fulfills its pumping function.

In this second embodiment, the rotatory force is applied to the blood in casing 41 by rocking rocker 45 with the circular cross section in the casing. By doing this, kinetic energy can be given to the blood sucked in through the central portion of casing 41, so that the blood can be discharged through the outlet portion, which is attached to casing 41 so as to extend tangent to the circular cross section of the casing.

Thus, rocker 45 of a simple shape can serve as a blood pump when it is only rocked in the aforementioned manner. Accordingly, the blood pump can be reduced in cost, so that it may be readily used as a disposable unit. Since the blood contacting portion of the pump, that is, pump chamber 40, is an only partially modified simple vessel, there is no problem on sealing. The internal configuration of the pump is simple, and the inner surface can be easily smoothed. Therefore, a turbulent or stagnant flow, which may destroy or coagulate the blood, cannot be easily caused. Thus, the pump can be used for a long period of time. Since the pump is of the turbo-type, moreover, pump chamber 40 can be reduced in capacity, and the pump can be implanted in a patient's body.

Figure 8:
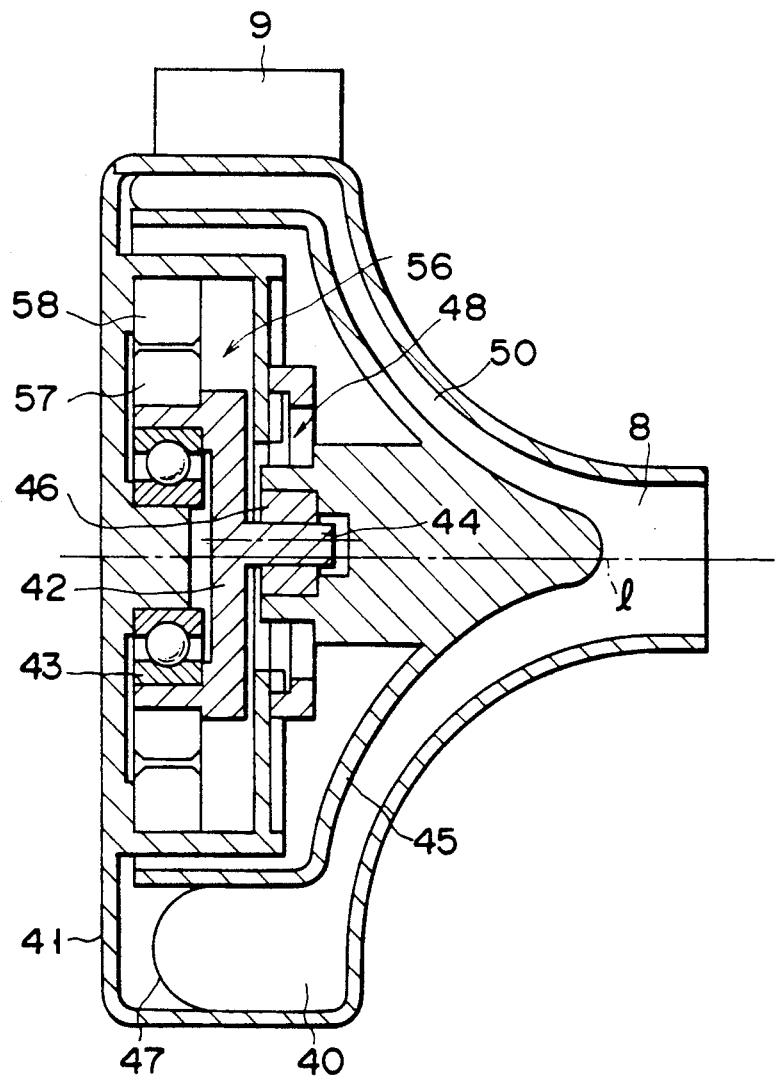
FIG. 8 is a longitudinal sectional view showing a modification of the medical pump according to the second embodiment.

FIG. 8 shows a modification of the medical pump according to the second embodiment. This modification is particularly characterized in the configuration of a passage defined between the inner surface of casing 41 and the outer surface of rocker 4 and extending from inlet port 8 to pump chamber 40, as shown in FIG. 8. More specifically, that portion of casing 41 corresponding inlet port 8 has the shape of a truncated cone. Likewise, that portion of rocker 45 corresponding to port 8 is conical. Thus, trumpet-shaped passage 50 is formed extending from the side of inlet port 8 to outlet port 9.

In this modification, therefore, when rocker 45 rocks in casing 41, a rotatory force acts on the blood in casing 41, so that the blood turns around. As the blood flows through trumpet-shaped passage 50, which extends from the side of inlet port 8 to outlet port 9, it is gradually given kinetic energy, starting from the region near inlet port 8.

Figure 10:
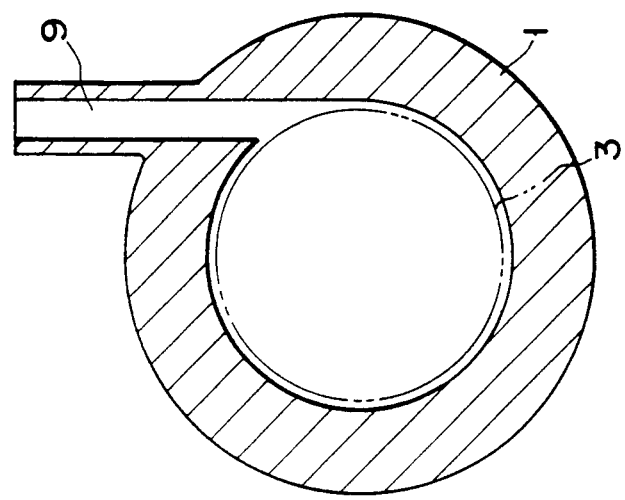
FIG. 10 is a cross-sectional view of a casing shown in FIG. 9.
Figure 9:
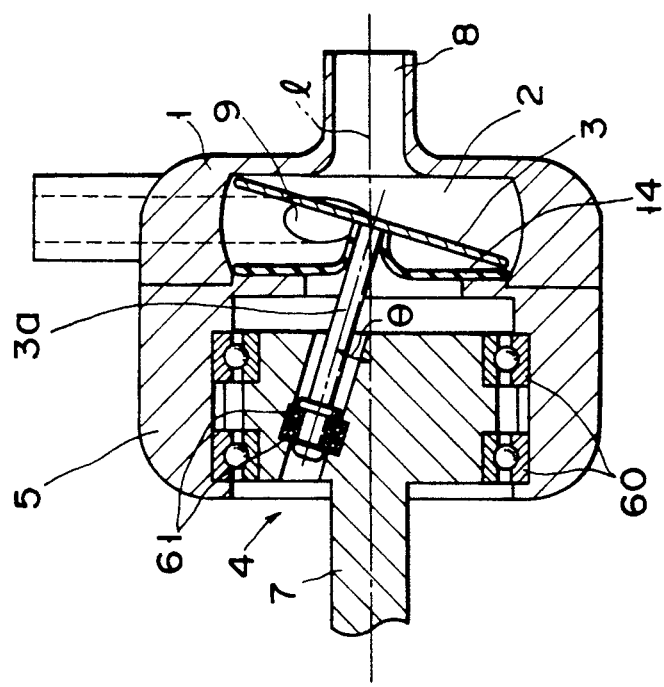
FIG. 9 is a longitudinal sectional view of a medical pump according to a third embodiment of the present invention.

FIGS. 9 and 10 show a medical pump according to a third embodiment of the present invention.

This medical pump comprises substantially flat cylindrical housing 1 which defines pump chamber 2 therein. Housing 1 has inlet port 8, situated near central axis 1 of chamber 2, and outlet port 9 extending tangent to a peripheral wall which defines chamber 2.

Disk-shaped precessional rocker 3 is disposed in pump chamber 2. The diameter of rocker 3 is substantially equal to that of pump chamber 2. Rotating shaft 3a is attached to the center of rocker 3 so as to extend at right angles thereto. Rocker 3 is driven by means of precessional mechanism 4.

The following is a description of precessional mechanism 4 according to the third embodiment.

A pair of first bearings 60 are attached to body 5 which is integral with housing 1. Motor shaft 7, which is connected to a drive motor, is rotatably attached to first bearings 60. Rotating shaft 3a of rocker 3 is inclined at angle $\theta$ to central axis 1 of pump chamber 2. The free end of shaft 3a is rotatably attached to second bearings 61 set in motor shaft 7. Seal 14, made of an elastic film such as polyurethane elastomer, is provided between rotating shaft 3a and housing 1, whereby rocker 3 is restrained from rotating in chamber 2. The inner surface of the wall which defines chamber 2 and the whole surface of rocker 3 are coated with an antithrombotic material.

The following is a description of the operation of the medical pump according to the third embodiment.

First, the motor (not shown) is rotated, so that motor shaft 7 rotates. As shaft 7 rotates in this manner, rotating shaft 3a is urged also to rotate. However, the rotatory motion of rocker 3 is prevented by seal 14, so that rocker 3 makes a precessional motion. When rocker 3 makes the precessional motion in housing 1, a rotatory force acts on the blood filling pump chamber 2 in housing 1, so that the blood flows rotating in the same direction as the precessional motion. Thus, the blood can be transported in the same manner as in the preceding embodiments.

Since the medical pump of this third embodiment has a simple construction, it can be reduced in manufacturing cost, and improved in reliability.

Figure 11:
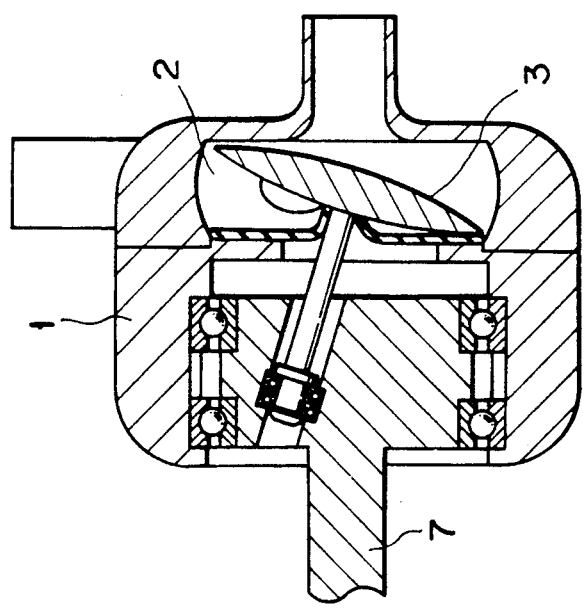
FIG. 11 is a longitudinal sectional view showing a first modification of the medical pump according to the third embodiment.

FIG. 11 shows a first modification of the third embodiment. In this first modification, rocker 3 is in the form of a disk having smooth spherical surfaces. Since both surfaces of rocker 3 are spherical, the blood in pump chamber 2 can flow smoothly, so that the blood feeding efficiency is higher.

Figure 12:
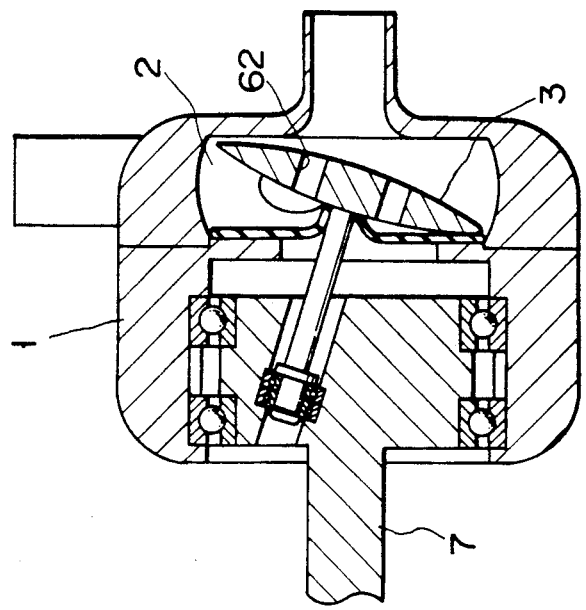
FIG. 12 is a longitudinal sectional view showing a second modification of the medical pump according to the third embodiment.

FIG. 12 shows a second modification of the third embodiment. In this second modification, a plurality of through holes 62 are bored through rocker 3. In this arrangement, the blood flows through holes 62 as rocker 3 makes a precessional motion.

Figure 13:
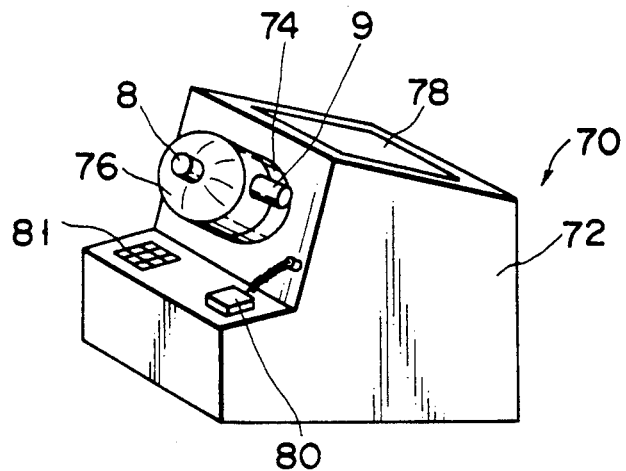
FIG. 13 is a perspective view of a pump system incorporating a medical pump according to a fourth embodiment of the present invention.
Figure 14:
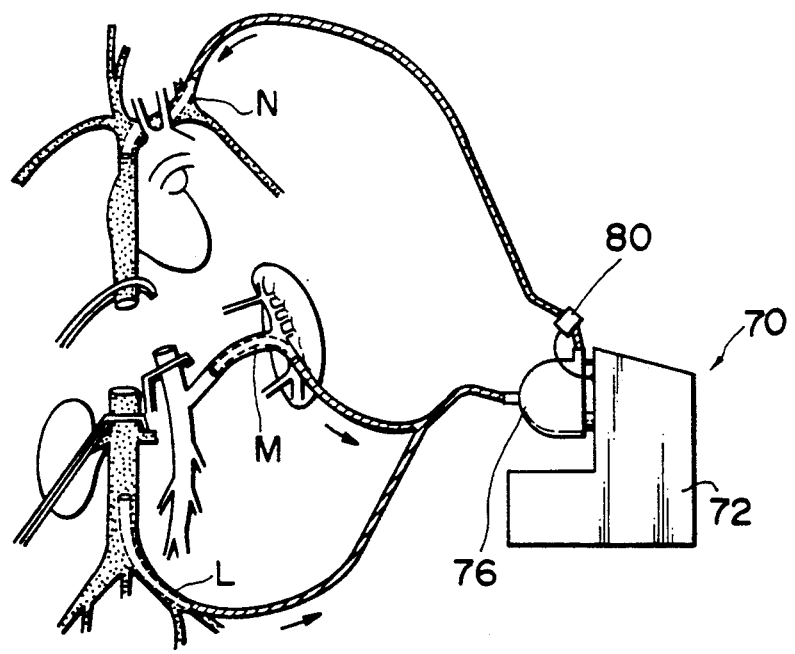
FIG. 14 is a diagram showing a state in which the pump system is attached to a patient's body.

FIGS. 13 to 18 show a medical pump according to a fourth embodiment of the present invention. In this fourth embodiment, the medical pump of the invention is applied to pump system 70, which is used as a by-pass between the left external jugular vein (N) and the combination of the inferior vena cava (L) and the portal vein (M), in the body of a liverless recipient under liver transplantation, as shown in FIG. 14.

FIG. 13 is a general view of pump system 70. System 70 comprises control unit 72 and pump head 76 removably mounted on unit 72 by means of attachment mechanism 74. Control unit 72 is provided with setting/display section 78, pressure/flow sensor 80, and operation keys 81. Section 78 is used to set pump drive conditions and display monitored drive conditions. Sensor 80 detects blood delivery.

Figure 15:
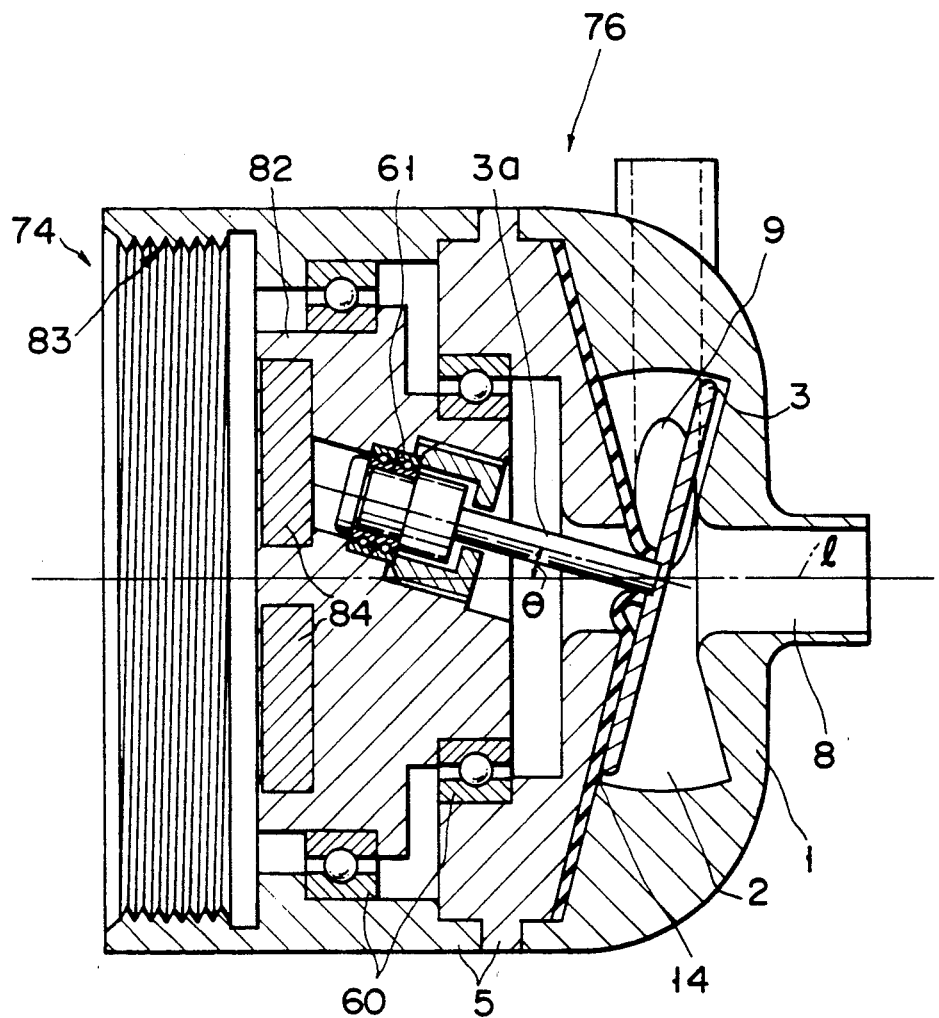
FIG. 15 is a longitudinal sectional view of a pump head of the medical pump according to the fourth embodiment.

FIG. 15 shows a profile of pump head 76. In head 76, right and left side walls of pump chamber 2 defined by casing 1 are formed so that they extend substantially parallel to the surfaces of rocker when the rocker rocks.

Rotating body 82 is rotatably attached to body 5 by means of first bearing 60. A plurality of magnets 84 are located on the back of body 82 so that opposite magnetic poles are arranged alternately. Formed at the rear portion of body 5 is attachment screw 83 which constitutes attachment mechanism 74 for the attachment on control unit 70.

An attachment screw (not shown), to which attachment screw 83 of pump head 76 can be threadedly fixed, is formed on that portion of control unit 70 to which head 76 is attached. When pump head 76 is mounted on control unit 70, a plurality of electromagnets (not shown) are arranged facing magnets 84 of head 76.

In the medical pump according to the fourth embodiment, if a suitable rotational frequency is set by means of control unit 70, the electromagnets successively change their polarity, thereby attracting or repelling magnets 84 of pump head 76. Thereupon, rotating body 82 rotates, and rocker 3 is rocked by means of a precessional mechanism, thereby feeding blood.

Thus, the pump according to this embodiment can stand prolonged used without entailing hemolysis or coagulation during blood delivery. Since the pump head section is designed for removable mounting, the pump head can be used as a disposable unit. Thus, sterilization of the pump is easy, and the safety is improved.

Further, the aforesaid special configuration of the pump chamber enables efficient fluid feeding.

Figure 16:
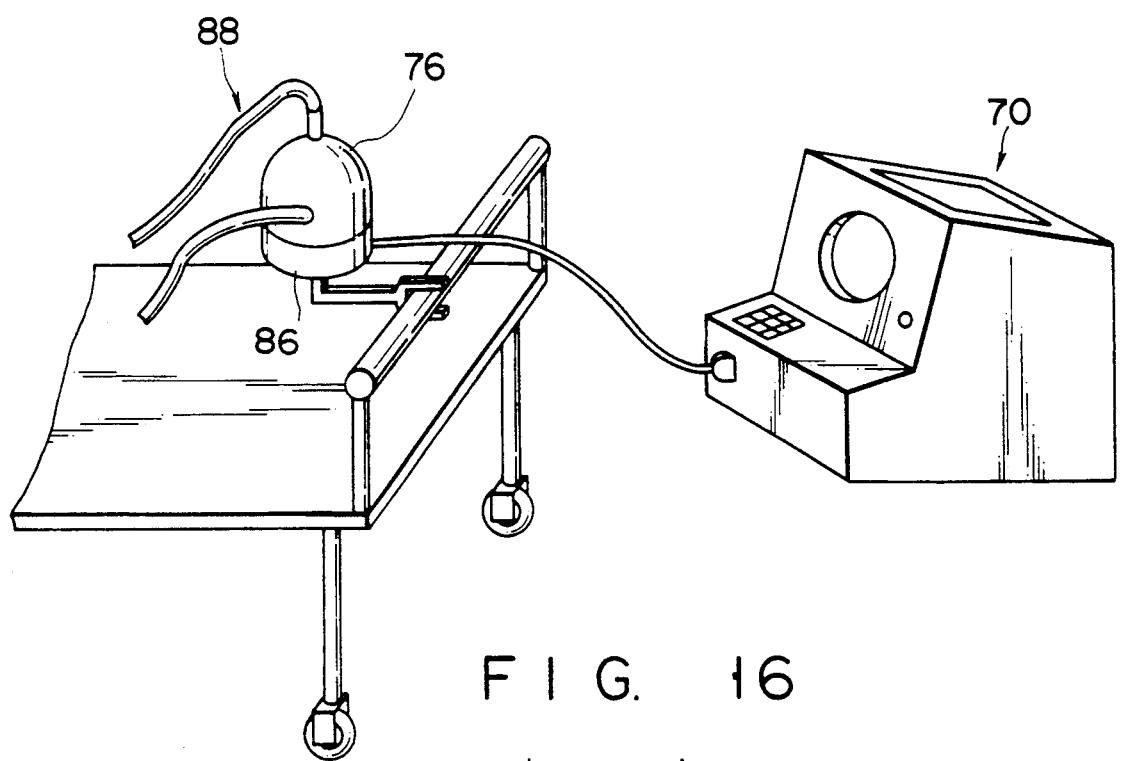
FIG. 16 is a perspective view showing an alternative application of the medical pump according to the fourth embodiment.

The blood pump according to the fourth embodiment is not limited to the pump system shown in FIG. 13. Alternatively, it may be applied to an artificial dialyzator, heart-lung machine, ECMO, artificial liver, or any other extracorporeal circulation system. As shown in FIG. 16, moreover, pump unit 88, formed of pump head 76 and drive motor 86, may be provided independently of control unit 70. In this case, pump unit 88 ma be set beside a bed or operating table on which the patient lies, for example.

Figure 17:
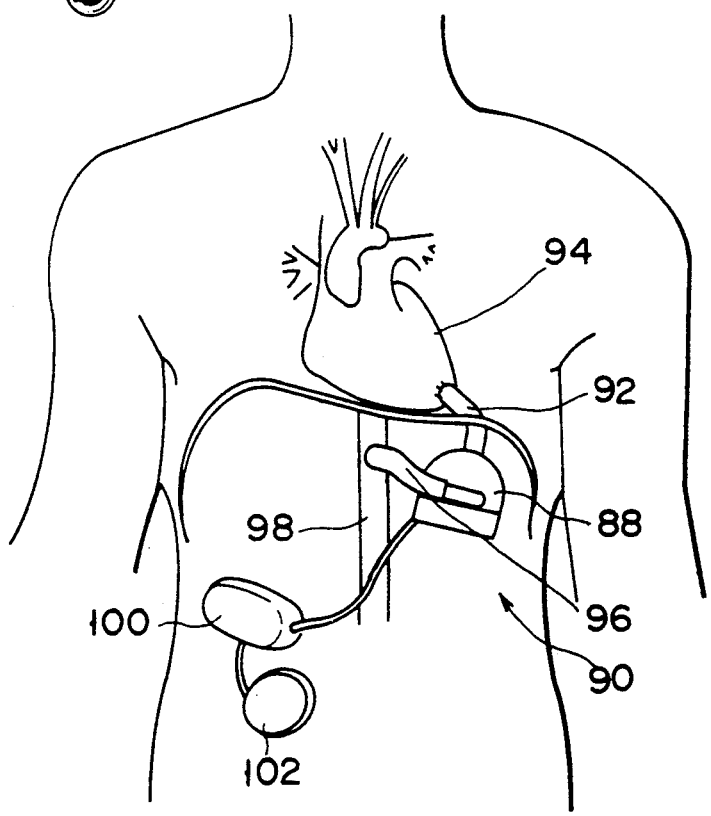
FIG. 17 is a diagram showing a state in which a medical pump according to a modification of the fourth embodiment of the present invention is set in a patient's body.

FIGS. 17 and 18 show implantation-type artificial heart 90 as an application of the pump according to the fourth embodiment.

FIG. 17 shows the whole system which incorporates artificial heart 90. Inlet port 8 of blood pump 88, which constitutes this system, is connected to heart 94 by means of inlet tube 92. Outlet port 9 of pump 88 is connected to inferior aorta 98 by mean of outlet tube 96. This system further comprises control section 100 and intracorporeal transformer 102. Control section 100 is used to control the drive of a motor attached to the bottom portion of blood pump 88. Transformer 102 serves to transfer a signal and energy to and from a extracorporeal transformer (not shown).

FIG. 18 shows a profile of the blood pump described above. A description of pump chamber 2 and precessional mechanism 4 is omitted, since these elements are constructed in the same manner as their counterparts in the foregoing embodiments. Rotating body 82, which is rotatably fitted with rotating shaft 3a of blood pump 88, is connected to drive motor 104 inside body 5. Motor 104 is connected to control section 100 by means of cable 106. The outer surface of pump 90 is coated with coating layer 108 for improved histocompatibility.

In the blood pump according to this modification, intracorporeal transformer 102 receives the signal and energy from the extracorporeal transformer, and drive motor 104 rotates in response to an output signal from control section 100. Thus, blood is fed nonpulsatively. Signals indicative of the drive conditions of the pump are delivered to the extracorporeal transformer, so that the drive conditions of the artificial heart can be externally monitored.

In this modification, moreover, the blood pump is stuffed in the body cavity. Alternatively, however, a pair of pumps (for the right and left heart systems) may be combinedly implanted in the thoracic cavity after extracting the heart.

Figure 19:
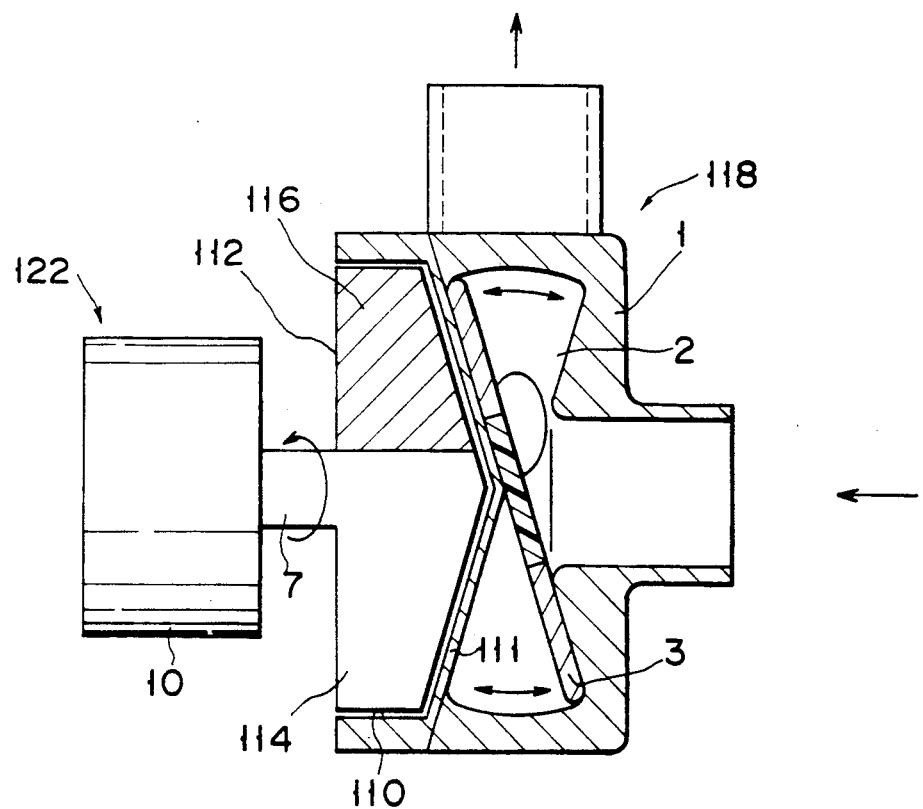
FIG. 19 is a longitudinal sectional view of a medical pump according to a fifth embodiment of the present invention.

FIG. 19 shows a medical pump according to a fifth embodiment of the present invention. In this fifth embodiment, pump unit 118 having pump chamber 2 and driving unit 122 including drive motor 10 are formed independently of each other.

As shown in FIG. 19, disk-shaped rocker 3, made of a magnetic material such as iron, is housed in chamber 2 defined in casing 1. Chamber 2 has a profile which extends from the central portion thereof toward the peripheral portion. The surface of rocker 3 is coated with an antithrombotic material. Rotating head 112, which is connected to motor shaft 7 of drive motor 10, is fitted in recess 110 formed in the proximal portion of casing 1. Head 112 is composed of nonmagnetic material portion 114 and permanent magnet portion 116. Magnet portion 116 may be either pole, north or south.

In this arrangement, a magnetic force from the magnetic portion of rotating head 112 acts on disk-shaped rocker 3 in chamber 2 through partition wall 111 of the chamber, thus forming a magnetic coupling. As head 112 rotates, therefore, rocker 3 in chamber 2 rocks.

Due to the use of the magnetic coupling, in the medical pump according to the fifth embodiment, chamber 2 requires no seal portion, so that the construction is simple. Since the interior of the pump chamber is completely isolated from the outside, moreover, the safety is improved. Further, the pump unit may be used as a disposable unit. Rocker 3 can be rotated without exerting any influence on the performance of the pump.

Figure 20:
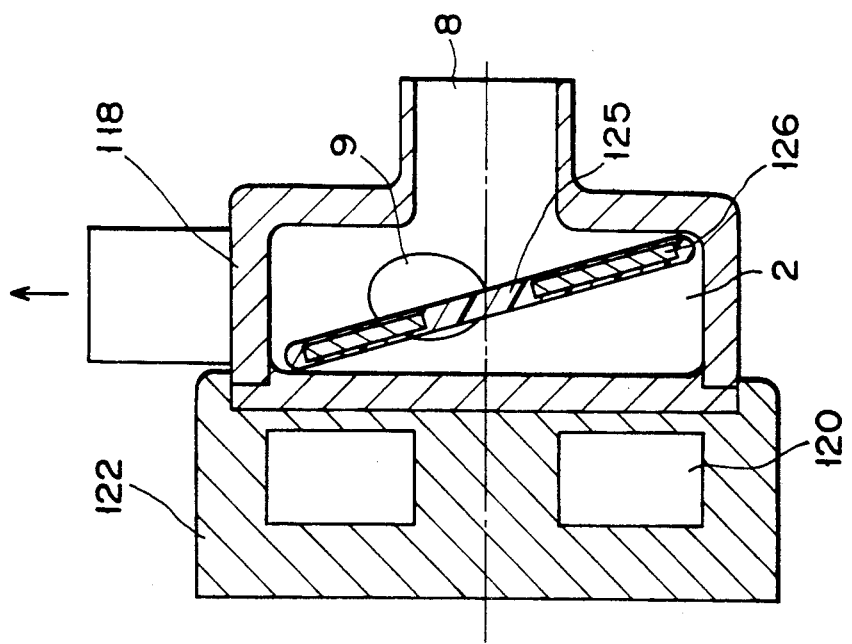
FIG. 20 is a longitudinal sectional view showing a first modification of the medical pump according to the fifth embodiment.
Figure 23:
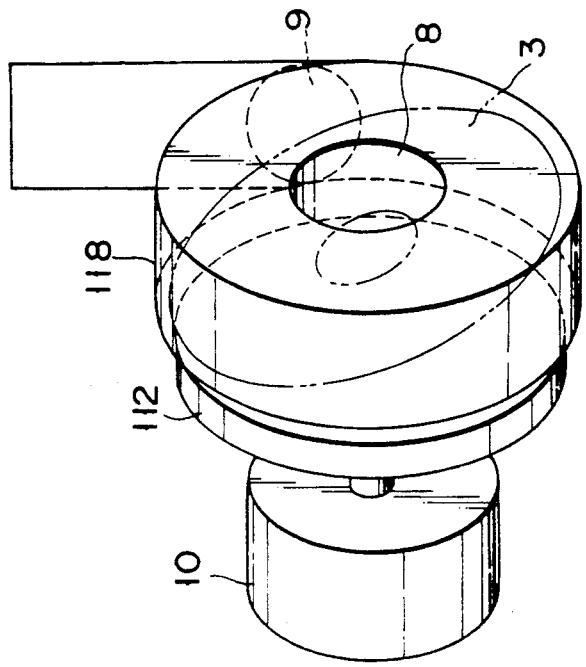
FIG. 23 is a diagrammatic view of the medical pump shown in FIG. 22.

FIG. 20 shows a first modification of the fifth embodiment. In this modification, pump unit 118 and driving unit 122, which includes electromagnet unit 120, are formed independently of each other. A plurality of electromagnets are arranged in driving unit 122 so that their polarity can be successively changed.

Meanwhile, rocker 3, which is housed in chamber 2 of pump unit 118, is formed by embedding permanent magnet 126 in circular plate 125. The surface of rocker 3 is coated with an antithrombotic material.

In this first modification, rocker 3 can be rocked by successively changing the polarity of the electromagnets of electromagnet unit 120. As in the fifth embodiment, the pump unit may be used as a disposable unit.

Figure 21:
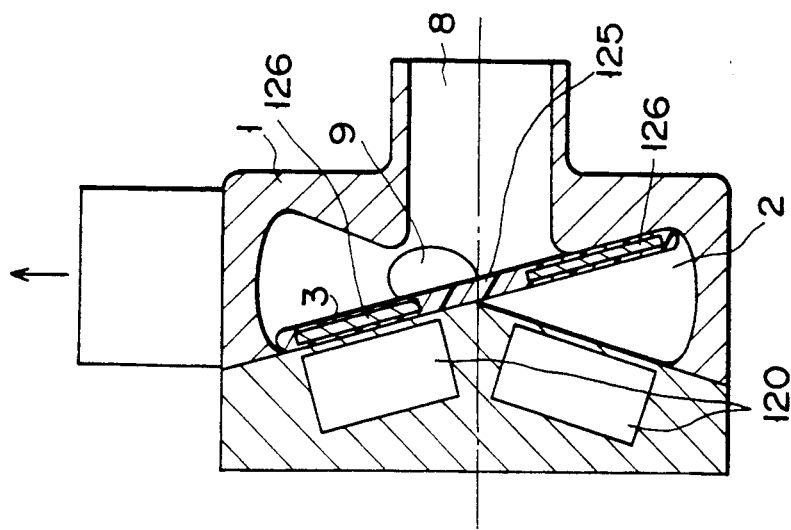
FIG. 21 is a longitudinal sectional view showing a second modification of the medical pump according to the fifth embodiment.

FIG. 21 shows a second modification of the fifth embodiment. In this second modification, the pump unit is not independent of the driving unit, and electromagnet unit 120 is embedded in the proximal portion of casing 1 having chamber 2 therein. Chamber 2 has a profile which extends from the central portion thereof toward the peripheral portion. Rocker 3 is formed in the same manner as in the first modification.

Also in the second modification, rocker 3 can be rocked by successively changing the polarity of a plurality of electromagnets of electromagnet unit 120.

FIGS. 22 to 25 show a third modification of the fifth embodiment. This third modification utilizes an effect such that the corresponding poles of a permanent magnet of a driving unit and a permanent magnet of a rocker repel one another, while their opposite poles attract one another.

Ring-shaped rocker 3 is housed in chamber 2 of pump unit 118. Rocker 3 is formed of a permanent magnet having axial polarity, and its surface is coated with an antithrombotic material.

Figure 22:
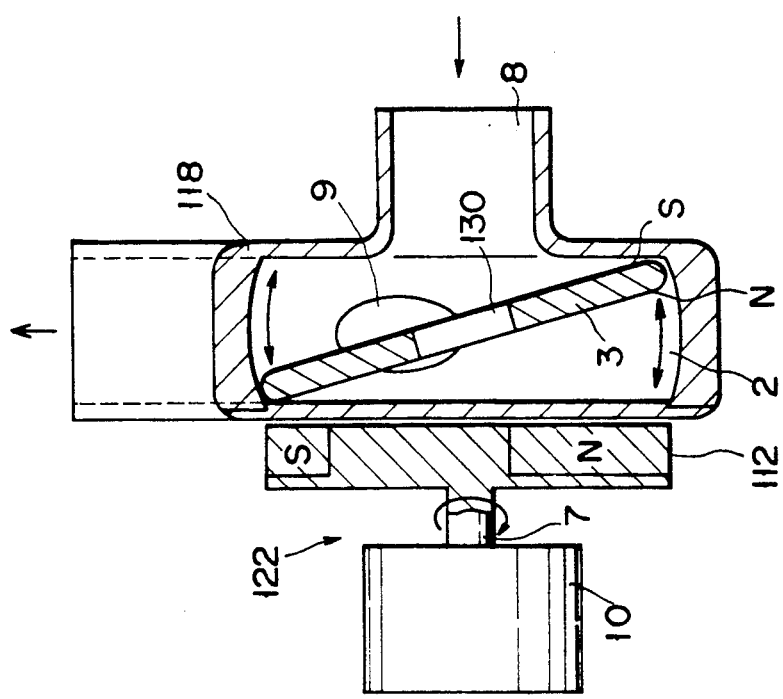
FIG. 22 is a longitudinal sectional view showing a third modification of the medical pump according to the fifth embodiment.

Meanwhile, disk-shaped rotating head 112 is mounted on rotating shaft 7 of drive motor 10, and a permanent magnet is disposed also in head 112. The permanent magnet of head 112 has poles arranged in the diametrical direction of the head. Thus, the corresponding poles of the permanent magnet of rotating head 112 and the permanent magnet of rocker 3 repel one another, while their opposite poles attract one another, so that rocker 3 can be kept tilted in one direction, as shown in FIG. 22. Accordingly, rocker 3 can be caused to process by rotating the rotating head of motor 10.

Figure 24:
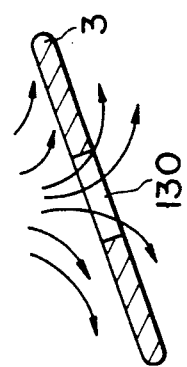
FIG. 24 is a diagram for illustrating the operation of a rocker shown in FIG. 22.

In this third modification, rocker 3 can be rotated without exerting any influence on the performance of the pump. As shown in FIG. 24, moreover, hole 130 is formed in the center of rocker 3 so that the rocker is ring-shaped. Therefore, blood can be delivered sufficiently to the back side of rocker 3.

A medical pump of the present invention is not restricted to the aforemention blood pump, and may be applied to, for example, a pump for circulating a dialysis liquid, a temperature-controlled pump for liquid circulation in a heat exchanger, such as the artificial lungs, and a pump for recycling-liquid circulation in an organ liquid-recycle maintaining device.

It is to be understood that the present invention is not limited to the embodiments and modifications described above, and that various changes and modifications may be effected therein by one skilled in the art without departing from the scope or spirit of the invention.

What is claimed is:

1. A medical pump comprising:
   a casing having a pump chamber defined by side walls and a peripheral wall;
   an inlet port provided on one of the side walls of said casing;
   an outlet port formed tangentially with respect to the peripheral wall of said casing;
   a disk arranged in said pump chamber substantially coaxially with an inner peripheral surface thereof having a central axis, a center of said disk being located at substantially a center of said pump chamber;
   a rocking shaft having an end fixed to the center of said disk, the longitudinal angle with respect to the central axis of said pump chamber;
   disk driving means for rocking said disk and having a rotation center axis, said disk driving means being rotatably connected to said rocking shaft, and having a driving body rotatably mounted on said casing; and
   said disk being arranged to have its center on the rotation center axis of said disk driving means such that said disk is rocked around its center.

2. A medical pump according to claim 1, further comprising;
   sealing means for sealing between said pump chamber and said disk driving means.

3. A medical pump according to claim 1, wherein said casing has a front portion separated in respect of a plane surface continuous to the other side wall on which said driving means is connected.

4. A medical pump according to claim 3, further comprising sealing means fixed between the surface of the other side wall and said disk.

5. A medical pump according to claim 1, wherein said disk has a through hole opened to both sides thereof.

6. A medical pump according to claim 5, wherein the through hole of said disk is provided near said rocking shaft.

7. A medical pump according to claim 1, wherein both surfaces of said disk are smooth and spherical.

8. A medical pump according to claim 1, wherein
   said disk driving means has a driving source and said driving body has a rotary shaft whose one end portion is connected to said rocking shaft, and another end portion of said rotary shaft is connected to said driving source,
   the one end portion of said rotary shaft having a hole tilted at a predetermined angle, for housing an end of said rocking shaft which is opposite to said end fixed to the center of said disk, and
   said rocking shaft is rotatably mounted in said tilted hole by a bearing for regulating the vibrations of said rocking shaft.

9. A medical pump according to claim 1, wherein
   said disk driving means has a driving source and said driving body has a rotary shaft whose one end portion is connected to said rocking shaft, and another end portion of said rotary shaft is connected to said driving source,
   the one end portion of said rotary shaft having a hole tilted at a predetermined angle, for housing an end of said rocking shaft which is opposite to said end fixed to the center of said disk, and
   said rocking shaft being in contact with only one bearing, said one bearing being mounted in said tilted hole for receiving the rocking shaft to regulate the vibrations thereof.

* * * * *